United States Patent
Roach et al.

(10) Patent No.: US 7,593,557 B2
(45) Date of Patent: Sep. 22, 2009

(54) METHODS OF SIGNAL PROCESSING OF DATA

(76) Inventors: Daniel E. Roach, c/o Faculty of Medicine, University of Calgary, Calgary AB (CA) T2N 4N1; Henry J. Duff, c/o Faculty of Medicine, University of Calgary, Calgary AB (CA) T2N 4N1; Robert S. Sheldon, c/o Faculty of Medicine, University of Calgary, Calgary AB (CA) T2N 4N1

( * ) Notice: Subject to any disclaimer, the term of this patent is extended or adjusted under 35 U.S.C. 154(b) by 944 days.

(21) Appl. No.: 11/017,929

(22) Filed: Dec. 22, 2004

(65) Prior Publication Data
US 2006/0136414 A1     Jun. 22, 2006

(51) Int. Cl.
G06K 9/00      (2006.01)
A61B 5/0452    (2006.01)

(52) U.S. Cl. .................. 382/128; 382/240; 600/521
(58) Field of Classification Search ............... 382/128, 382/130–132, 240; 702/67; 707/6; 708/5; 600/508, 521
See application file for complete search history.

(56) References Cited

U.S. PATENT DOCUMENTS

| | | | |
|---|---|---|---|
| 5,933,818 | A  | 8/1999 | Kasravi et al. |
| 6,236,757 | B1 | 5/2001 | Zeng et al. |
| 6,430,547 | B1 | 8/2002 | Busche et al. |
| 6,470,333 | B1 | 10/2002 | Baclawski |
| 6,675,164 | B2 | 1/2004 | Kamath et al. |
| 2002/0129342 | A1 | 9/2002 | Kil et al. |

*Primary Examiner*—Duy M Dang
(74) *Attorney, Agent, or Firm*—Anthony P. Lambert

(57) ABSTRACT

A method of signal processing of data using a computer by generating a symbolic map of the data using at least one wavelet transform, identifying target sequences in the symbolic map; and processing the data with reference to the target sequences to obtain waveform prognostic indicators.

9 Claims, 4 Drawing Sheets

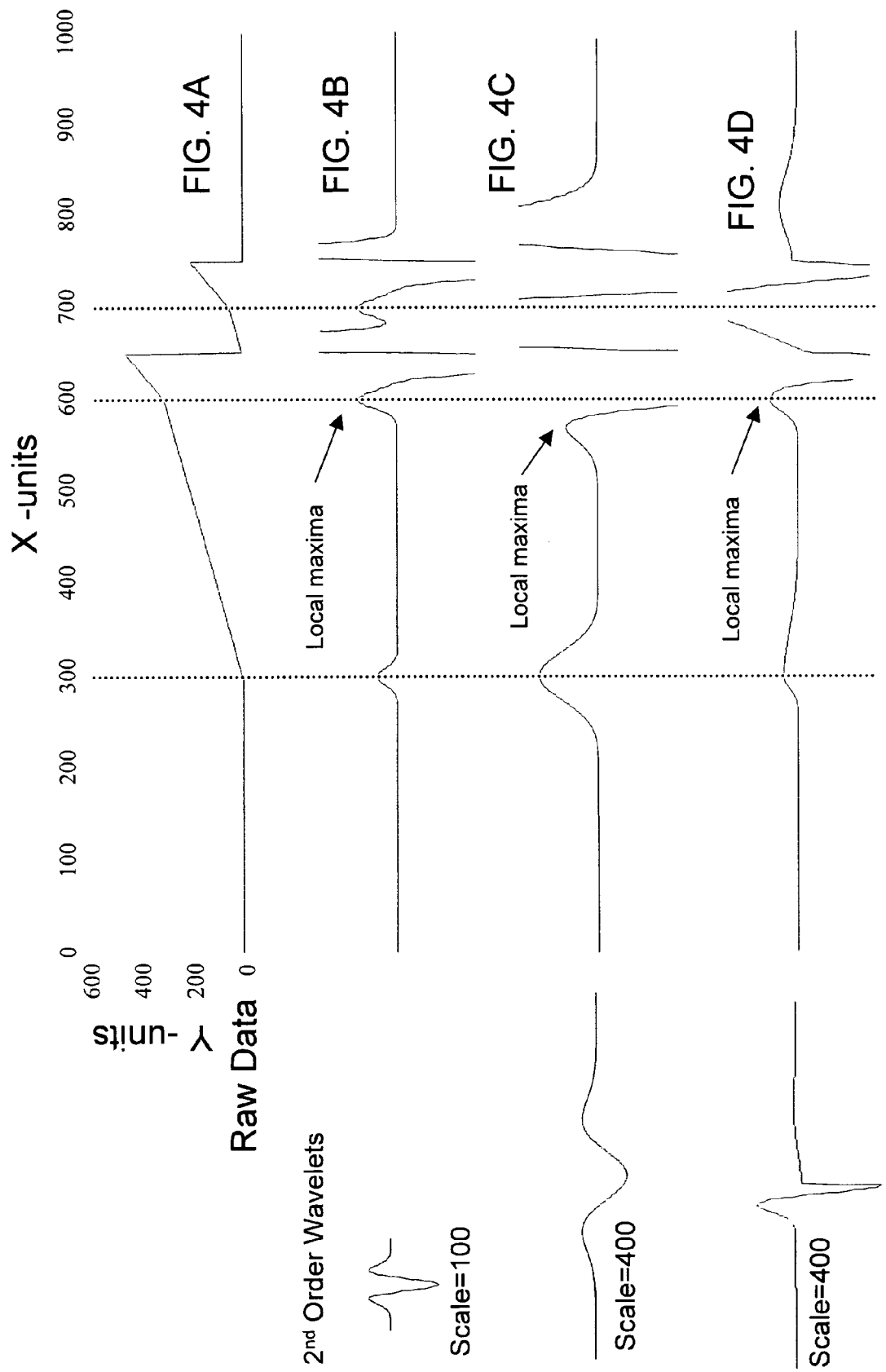

METHODS OF SIGNAL PROCESSING OF DATA

BACKGROUND OF THE INVENTION

As techniques for producing data become more refined and the quantity of data increases, methods of data mining are becoming more important.

For example, U.S. Pat. No. 6,675,164 (Kamath) describes a data mining system that uncovers patterns in data, including identifying relevant features of objects and recognizing patterns based on the features. Kamath also describes use of wavelet transforms in processing the data in relation to pre-processing operations such as filtering and noise reduction.

U.S. published patent application 2002/0129342 (Kil) teaches a data mining system that mainly deals with insertion of custom algorithms in a data mining process, and discloses use of wavelet transforms in a pre-processing step to extract features from the data.

U.S. Pat. No. 6,470,333 (Baclawski) teaches use of wavelet transforms in a feature extractor of a knowledge extraction system. U.S. Pat. No. 6,430,547 (Busche) also discusses data mining. U.S. Pat. No. 5,933,818 (Kasravi) teaches reducing data to clusters and obtaining correlations from the clustered data that represent knowledge.

SUMMARY OF THE INVENTION

Despite these data mining techniques there remains a need for a tool that assists in discovering unrecognized prognostic entities in data such as ECG data. Existing technologies are not designed for discovery. According to an aspect of the invention, there is therefore provided a method of signal processing of data using a computer by generating a symbolic map of the data using at least one wavelet transform, identifying target sequences in the symbolic map; and processing the data by reference to the target sequences to obtain waveform prognostic indicators. These and other aspects of the invention are described in the detailed description of the invention and claimed in the claims that follow.

BRIEF DESCRIPTION OF THE DRAWINGS

There will now be described preferred embodiments of the invention, with reference to the drawings, by way of illustration only and not with the intention of limiting the scope of the invention, in which like numerals denote like elements and in which:

FIGS. 4A-4D show a data trace and three transforms of the data set using different wavelets to discriminate features in the data trace.

DETAILED DESCRIPTION OF PREFERRED EMBODIMENTS

In this patent document, the word "comprising" in a claim does not exclude the possibility of other elements being present. In addition, a reference to an element by the indefinite article "a" does not exclude the possibility that more than one of the elements is present.

The input data on which the invention operates may be any input data having distinct recurring meaningful elements. The data may be for example medical sensor data such as ECG data, geophysical data such as seismic data or financial data such as stock prices. The data is typically a time series, where the data points represent samples from a sensor of a physical parameter, but may be any kind of multi-dimensional data as for example 2-dimensional data. The exemplary embodiment is described in relation to ECG data.

Figure 1:
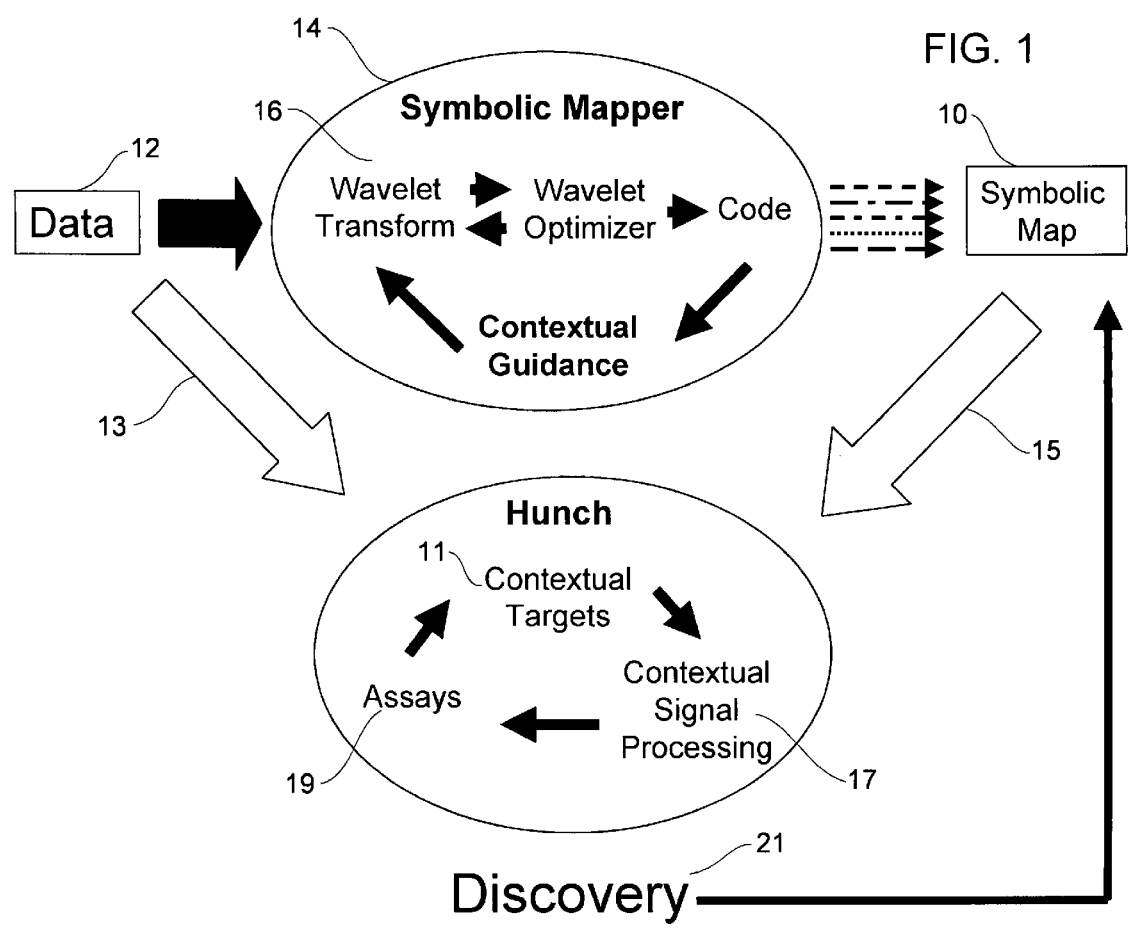
FIG. 1 is a schematic showing process steps according to an embodiment of the invention.

As shown in FIG. 1, the data is first processed to obtain a symbolic map 10 from the data 12. A symbolic map 10 is a symbolic sequence of recognized physical elements. In the case of medical sensor data, the physical elements may be recognized physiological elements, such as P and R waveforms. A symbolic mapper 14 is used to transform raw data 12 into a symbolic map 10, preferably based on expert prior knowledge. The transform is obtained by wavelet processing 16. A wavelet is convolved with the data to yield the symbolic map 10. The processing may occur in a computer of any suitable kind, and the symbolic mapper 14 itself is a program or part of a program stored in the computer. The symbolic map 10 comprises a series of symbols, such as P and R, and a location corresponding to each symbol. Various techniques such as intermodal entropy may be used to tune the wavelet to optimize symbol recognition. It is preferable to use an iterative graphical interface, such as provided by any of various graphical programs such as MATLAB™, to allow continuous iterative analysis of the symbolic map.

In the iterative process, a wavelet is first chosen based on knowledge of the type of data being used. Any kind of wavelet may be used. The characteristics of the wavelet that define the wavelet are the order and scale. For example, a Gaussian wavelet (zero order wavelet) or its first derivative (first order wavelet) or its second derivative (second order wavelet) may be used. The first order wavelet is useful for detecting specific slopes in the raw data, while a second order wavelet may be used for detecting changes in slope. The scale of the wavelet is selected based on the scale of the feature of interest in the raw data. Asymmetric wavelets may also be used for example where different parts of the wavelet have a different order or scale. Thus, for example, each of the wavelet may be independently scaled. Asymmetric wavelets are useful for detecting asymmetric features of the raw data.

A symbolic map is generated by transforming the raw data using the selected wavelet. The wavelet may then be tuned, if it is desirable to improve symbol recognition. Repeated tuning yields repeated symbolic maps, and the operator may also use contextual guidance to refine the wavelet, and re-iterate the wavelet transform until the symbolic map is optimized. Contextual guidance depends on the type of data being used. For example, if a data series is expected to have a specific recurring element, then the specific recurring element may be identified by optimizing the wavelet. A simple discriminator may be used to identify a specific symbol in the wavelet transform, such as a threshold test, window, or low pass or high pass filter on the magnitude of transformed data. Using MATLAB™ or some other graphical mathematical analysis software suite is useful for this processing since the software may readily be programmed to identify and display peaks in the transformed data that fall within a given range, or exceed a given value. Iterative graphical software is preferred so that the results of specific processing may be observed immediately upon processing.

Various numbers and combinations of wavelets may be used to transform the data and the discriminator applied to the resulting transforms to generate the symbolic map. Further, the discriminator may perform various logical operations. For example, the discriminator may apply a test such as: If at time T1, transform A of a set of data is greater than 1, and transform B of the set of data is greater than 0.5, then assign symbol X to time T1. The transformed data may be conditioned using any of a variety of mathematical operations before application of the discriminator, such as by computation of a sum, difference, time-shift or cross-correlation of one or more transforms of the raw data. For example, the discriminator may apply a test such as: If in a specified time window preceding symbol X, there is a value in the transformed data greater than 0.5, then assign symbol Y to the time at which the value occurred. In such a case where one symbol has a known relation to another and one of the symbols is more readily definable, a recognition hierarchy may be used in which one symbol is identified first and then information from the identification of that symbol used to find the other.

Figure 2:
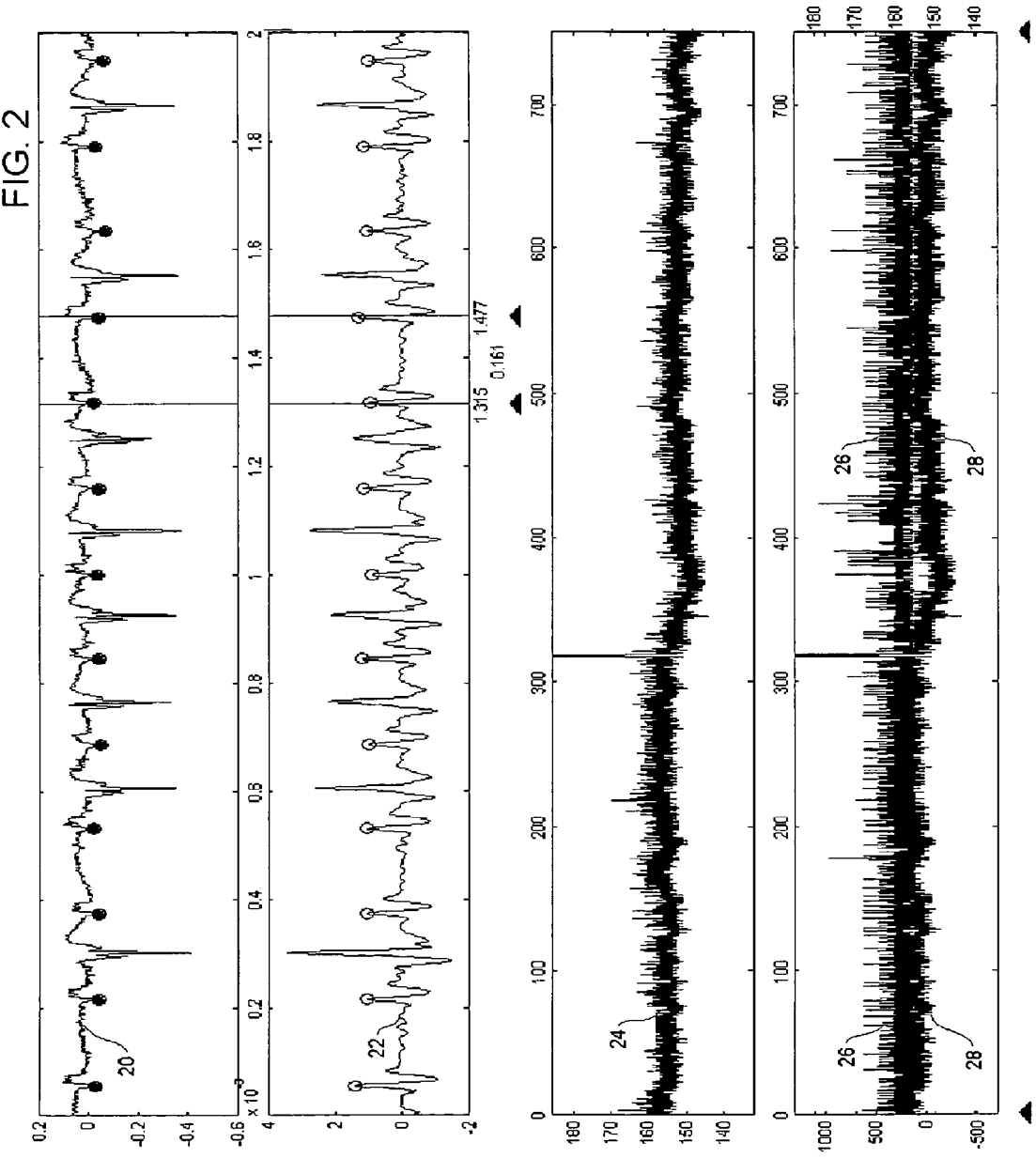
FIG. 2 shows a raw data trace, a transform of the raw data trace and statistical analysis of the raw data trace according to the invention.

An exemplary raw data series 20 of ECG data is shown in FIG. 2, upper trace. This ECG is processed with a wavelet to yield the wavelet transform in the trace 22 below the upper trace of FIG. 2. The wavelet identification in a program such as MATLAB™ may be readily shown in windows on the same screen if desired. In this specific example, a second order wavelet with a scale of 60 has been used to transform the raw data 20. Using a mathematical software suite, the transform 22 may be generated in milliseconds. Peaks in the transform 22 within a range of magnitude of about 1-2 have been circled automatically using the software. For the ECG data given, it is considered that these peaks represent the P portion of the ECG data. The R peaks can be obtained in like manner, although better discrimination of the R symbols is obtained using a first order wavelet. The resulting set of P and R symbols, identified by their corresponding occurrence times are the symbolic map. The occurrence time of a symbol may be identified in relation to a specific feature of the transformed data, such as the maximum value, or a specific feature of the raw data, such as a zero crossing or maximum slope.

Various properties of the transform may be tested to assist in verifying the accuracy of the symbol identification. As shown in FIG. 2, the trace 24 represents the time interval between P symbols in the raw data. A kink in the data starting around the time 300 is expected due to a known heart condition of the animal under observation and improves the confidence of the operator in the integrity of the symbolic map. The lowermost traces of FIG. 2 show both the R-R interval 26 and the P-P interval 28. When multiple wavelet transforms are used on the raw data, several transforms may be displayed at the same time, in a layered presentation. Such a display facilitates estimating the accuracy of the symbolic mapping.

Once a symbolic map is generated, all or part of the symbolic map is used to process the raw data or the transformed data. For example, a specific sequence of symbols may be used for further processing of the raw data. The further processing may include any mathematical operation, including various statistical analyses, such as averaging. The mathematical operation may be applied to the sequence of symbols. A specific sequence of symbols provides a context for subsequent signal processing. This part of the data mining process is referred to as Hunch in FIG. 1. A sequence of symbols forms a contextual target 11. The raw data 13 or the symbolic sequence 15 is then processed using the contextual target 11 to focus the processing 17. Once information has been acquired from processing 17, it may be evaluated in an assay 19. Depending on the information acquired during the assay 19, the contextual target 11 may be modified and then further processing 17 undertaken. From the assay 19, a discovery 21 may be made. A phase transition in the processed data may for example represent a discovery, as for example as shown in the lower trace of FIG. 2, where a change in R-R interval represents a physiological condition.

Figure 3:
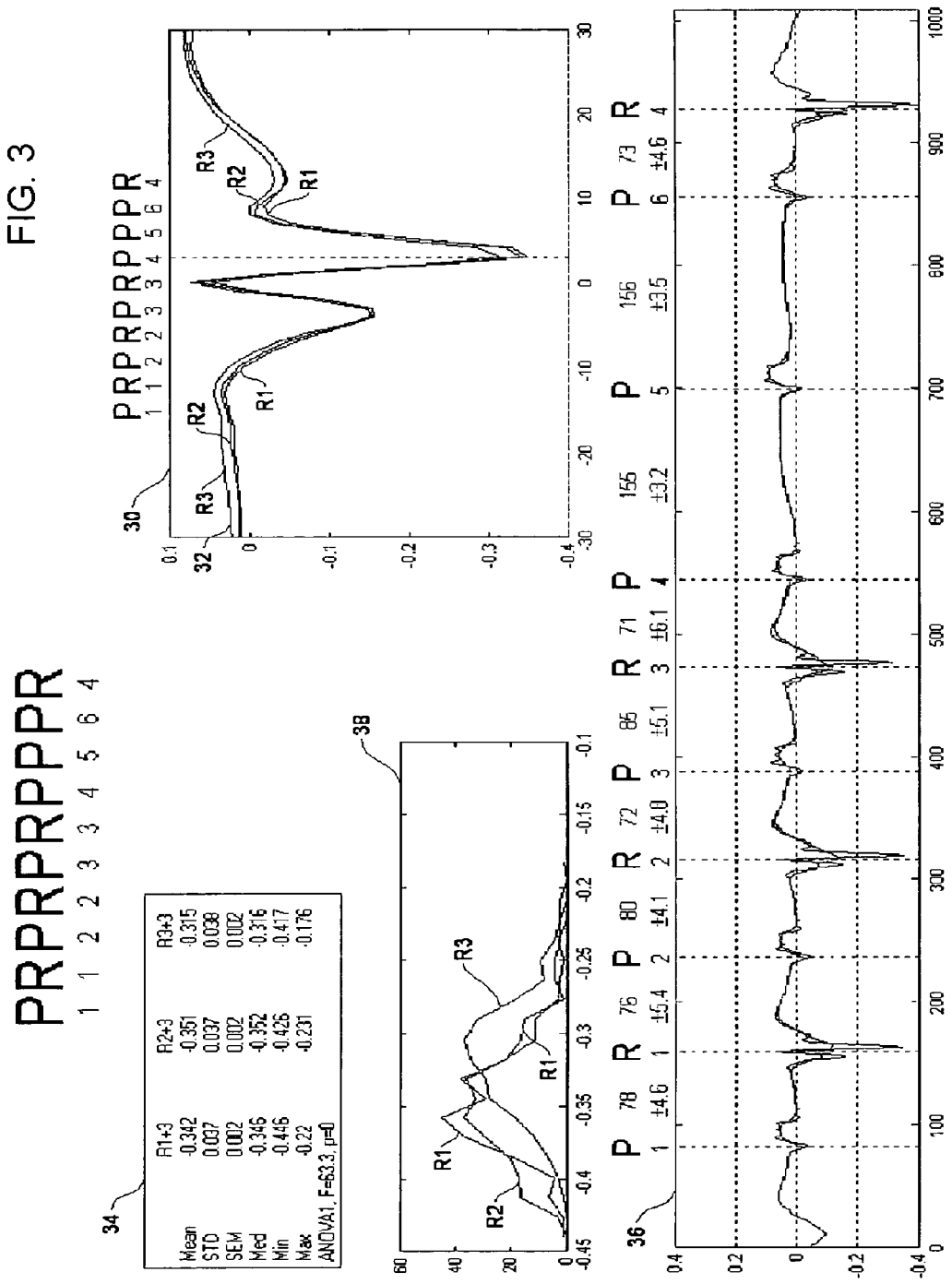
FIG. 3 shows several graphs displaying statistical analysis of the raw data based on the transform displayed in FIG. 2.

An example of contextual signal processing, in this case, contextual signal averaging, is shown in FIG. 3. In this case, a repeating sequence of symbols PRPRPRPPPR has been generated by transformation of raw ECG data in the manner shown in FIG. 2. Each P and R symbol is associated with a specific time location in the raw data, which in this case is chosen as the point of maximum slope. Once the target sequence PRPRPRPPPR is identified, all occurrences of the sequence may be found readily. In the example shown in FIG. 3, there are 244 occurrences. The symbols of the sequence may be further identified by their location in the sequence as P1, R1, P2, R2, P3, R3, P4, P5, P6 and R4. In the graph 30, the raw data in a window about each of the R1, R2 and R3 symbols of the symbol sequence have been averaged together after tying them to the same time location, which in this case corresponds to the point of maximum slope of the raw data. It can be seen that the early values of the raw data corresponding to the R3 symbol, indicated at 32, are significantly higher than the corresponding values of the raw data corresponding to the R1 and R2 symbols. Further statistical analysis, including the mean, standard deviation, SEM, median, maximum and minimum of the raw data corresponding to the R1, R2 and R3 symbols may be readily carried out using a mathematical software suite. A table 34 of these statistics for the ECG data of FIG. 2 is shown in FIG. 3 to the left of graph 30. The lower graph 36 of FIG. 3 shows an average of the raw data for the 244 PRPRPRPPPR sequences identified in FIG. 2. Graph 36 also shows the average time between P and R symbols, the average time location in the sequence and the standard deviation of the time between successive P and R symbols. Various statistical tests may be applied to the raw data or symbolic sequences. For example, a paired-T test may be applied to the raw data corresponding to successive pairs of R and/or P symbols to assess relative differences between the data, as for example between the R1 and R2 data. Histogram 38 in FIG. 3 is a histogram showing number of occurrences (y axis) of a given peak voltage (x axis) in the raw data for each of the R1 symbols, R2 symbols and R3 symbols. The statistical difference of the R3 value is significant in that it corresponds to a specific physiological event within the animal monitored, namely in this case that before the animal's hearts stops beating there is a transient decrease in sodium channel formation.

The symbolic sequence generates a lexicon that defines a macroscopic event. Although the example is given for a PRPRPRPPPR sequence, other sequences may be used depending on the type of data. In ECG data, the PR sequence alone is useful. A change in PR interval may be physiologically significant. Hence, contextual signal processing on raw data collected as P and R events may yield clinically significant information. In this case, the ECG data is first processed to yield a symbolic map containing P and R symbols according to the steps shown in FIG. 1. Next, contextual signal processing is applied to the raw data based on the P and R events. For example, P-P or R-R intervals may exhibit significant differences.

The process steps of generating a symbolic map followed by contextual signal processing using the symbolic map may also be applied to raw data generated after an induced event. An example of an induced event for ECG data is a large muscle contraction, which produces an alteration in the PR sequence. The response of the body to the large muscle contraction may be analyzed with contextual signal processing of the raw data by reference to the symbolic map.

After identifying the target sequence of interest, the target sequence may be further processed to refine the assay selection criteria based on features of the symbols such as interval times between target symbols; and/or wavelet transform values obtained for the target symbols. A particular symbol may have, for example, different shapes, and the processing of the data only applied to symbols that meet a selected shape criteria. In addition, interval time between symbols may reflect distinct physical states, or physiological states for medical sensor data. Data corresponding to specific symbols may be selected based on the interval time between symbols. Thus, for example, only data associated with symbols that have a specific symbol interval time might be processed and assayed.

Contextual signal processing therefore organizes raw data based on position in target symbol sequence (rather than in time) to produce an output, namely a discovery of potential worth. The assay step seeks to use contextual signal processing to numerically validate a hunch. To generate a symbolic map, a wavelet must be used, and in practice selected by an operator, that recognizes recurring components of raw waveform. An operator may need to tune the wavelet transform to optimize the mapping (e.g. sinus beat, PVC, APC). Context, such as knowledge of a relationship between the symbols, may assist in identifying symbols, for example in ECG data a p-wave precedes a qrs complex. Changing of the scale and order of the wavelet iteratively and concurrent observation of the resulting symbolic map may assist in symbol discrimination.

Gaussian-derived wavelet transforms provide two vital facets of information: 1) a quantitative measure of select local polynomial behaviour at select scales, and 2) a location where this polynomial behaviour is maximized. These local maxima and minima of the wavelet transform delineate those recurring instances of time when the raw data conforms to symbol-specific local morphometric criteria. In other words, the wavelet transform maxima and/or minima "mark" the times of the recurring symbols. In most instances, the order and scale of the delineating wavelet can be adjusted, and contextually applied, in an effort to optimally distinguish different recurring elements. However, there may instances when distinct entities yield similar recurring elements that are difficult to discriminate. Subtle changes to the Gaussian wavelets may facilitate discrimination.

FIGS. 4A-4D illustrate utility of different wavelets in feature discrimination. In the raw data trace of FIG. 4A, at X=300, there is a distinct change in slope, from slope=0 in the left neighborhood, to slope=1 in the right neighborhood. At X=600, the slope again increases from slope=1 in the left neighborhood to slope=3 in the right neighborhood. Note that this change in slope structure at X=600 is repeated again at X=700. FIG. 4B shows the wavelet transform produced using a scale=100 X-units and order=2 Gaussian wavelet. The wavelet is shown on the left. As expected, because the wavelet spans only 100 X-units, the wavelet transform for the two structures is the same, as evident by the similar wavelet transform values occurring at X=600 and X=700. Despite the similarity in the transforms of the two points, the structures at X=600 and X=700 may not represent the same entity, as for example the entity at X=600 may always have a wide slope=1 in the left neighborhood. Then, to distinguish the entity at X=600 from the entity at X=700, a wavelet of larger scale may be used, since the X=600 entity has discriminating information at the larger scales whereas the X=700 entity does not. If this large scale structure representing the entity from X=300 to X=650 is to be symbolically represented by the point of change in slope occurring at X=600, the local maxima of the larger scale wavelet will no longer be centered on the change in scale occurring at X=600. Instead, because the right neighborhood of the entity at X=600 is only 50 X-units wide, any wavelet of scale greater than 100 X-units will integrate beyond the right hand limit of the right neighborhood and thus the location and magnitude of the local maxima will be partially determined by whatever raw data is out there. FIG. 4C shows the wavelet transform for a $2^{nd}$ order wavelet of scale 400 X-units. The local maxima no longer occurs at X=600. Thus, we cannot accurately map this point of the entity. To address this problem, the wavelet used to transform the data may be asymmetric with left and right neighborhoods of unequal proportions, while maintaining the zero integral requirement for wavelets. FIG. 4D shows an asymmetric $2^{nd}$ order Gaussian wavelet at scale=400 X-units on the left, and the transform of the trace of FIG. 4A using this asymmetric wavelet. FIG. 4D shows how the asymmetric Gaussian wavelet of scale=400 X-units preserves the location of the change in slope at X=600. Thus, the asymmetry element of the wavelet is used to distinguish and correctly delineate the entity of interest.

The configuration of the wavelet may be readily adjusted using a graphic user interface (GUI) such as MATLAB™ used as the mapper. The user can quickly adjust this asymmetry and immediately see if there is a benefit, which will be revealed for example in the processed data, such as in a histogram. In an asymmetric wavelet, the left and right neighborhoods may be of discretely different scales or have a continuous change in scale from left edge of the left neighbourhood to the right edge of the right neighbourhood. Such Gaussian derived asymmetric scale varying wavelet thus uniformly change scale in going from left to right and may have utility in discriminating elements of a data trace.

The data mining system thus described is a tool for finding and verifying predictors of symbolic transitions. Hunch provides a framework for finding predictors of statistical truth about user-defined events. The framework facilitates easy refinement of predictors. It does this by visualizing recurring transitions and finding elements that predict the transitions. An operator may look at the raw and signal averaged raw data to refine the symbols required to define the transition. The data mining system therefore provides increased knowledge of system dynamics to find logical refinements that speed up the search process for statistical truth. In addition, even without increased knowledge, state transitions identified by the contextual signal processing provide useful information about the system.

The symbolic mapper, including the discriminator, sequence identifier and signal processor for processing the data using the symbol sequences are a set of instructions that are stored in a computer in computer readable media, and may be transferred from one computer to another via any suitable means such as over conventional computer to computer cables, wireless connection or via a physical disc. The instructions themselves computer language translations of the instructions contained in this patent document, may be easily programmed using software such as MATLAB™.

Immaterial modifications may be made to the embodiments described here out departing from the invention.

What is claimed is:

1. A method of signal processing of data using a computer, the method comprising the steps of:

acquiring a data signal comprising data points, where the data points represent samples from a sensor of a physical parameter and the data signal has distinct recurring elements that represent physical elements;

generating a symbolic map of the data signal by applying at least one wavelet transform to the data signal using the computer, the symbolic map corresponding to a sequence of physical elements represented within the data signal;

identifying target sequences in the symbolic map; and processing the data signal with reference to the target sequences to obtain waveform prognostic indicators.

2. The method of claim 1 in which processing the data signal with reference to the target sequences comprises applying statistical analysis to the data signal.

3. The method of claim 1 in which generating a symbolic map comprises applying multiple wavelet transforms to the data signal.

4. The method of claim 1 in which the method steps are carried out using iterative graphical software.

5. The method of claim 1 in which the data signal is an ECG data signal.

6. The method of claim 5 in which processing the data signal with reference to the target sequences comprises applying statistical analysis to the data signal.

7. The method of claim 6 in which processing the data signal with reference to the target sequences comprises averaging data corresponding to specific symbols in the target sequences.

8. The method of claim 1 in which the wavelet transform uses an asymmetric wavelet.

9. Computer readable media containing instructions for carrying out the steps of claim 1.

* * * * *